(12) United States Patent
Amaravadi et al.

(10) Patent No.: US 8,716,307 B2
(45) Date of Patent: May 6, 2014

(54) COMBINATION ANTINEOPLASTIC THERAPY

(75) Inventors: Ravi Kumar Amaravadi, Media, PA (US); Craig B. Thompson, Merion, PA (US)

(73) Assignee: The Trustees Of The University of Pennsylvania, Philadelphia, PA (US)

(*) Notice: Subject to any disclaimer, the term of this patent is extended or adjusted under 35 U.S.C. 154(b) by 50 days.

(21) Appl. No.: 13/319,604

(22) PCT Filed: May 4, 2010

(86) PCT No.: PCT/US2010/033514
§ 371 (c)(1),
(2), (4) Date: Nov. 22, 2011

(87) PCT Pub. No.: WO2010/132233
PCT Pub. Date: Nov. 18, 2010

(65) Prior Publication Data
US 2012/0129810 A1 May 24, 2012

Related U.S. Application Data

(60) Provisional application No. 61/177,697, filed on May 13, 2009.

(51) Int. Cl.
*A01N 43/42* (2006.01)
*A61K 31/44* (2006.01)
*A61K 31/47* (2006.01)
*C07D 491/00* (2006.01)
*C07D 498/00* (2006.01)
*C07D 515/00* (2006.01)
*C07D 215/38* (2006.01)

(52) U.S. Cl.
USPC .............. 514/291; 514/313; 546/89; 546/159

(58) Field of Classification Search
USPC .............................. 514/291, 313; 546/89, 159
See application file for complete search history.

(56) References Cited

U.S. PATENT DOCUMENTS

| | | | |
|---|---|---|---|
| 5,100,899 A | 3/1992 | Calne | |
| 5,362,718 A | 11/1994 | Skotnicki et al. | |
| 5,536,729 A | 7/1996 | Waranis et al. | |
| 5,989,591 A | 11/1999 | Nagi | |
| 2003/0153593 A1* | 8/2003 | Dukart et al. | 514/291 |
| 2005/0032834 A1* | 2/2005 | Kastan et al. | 514/313 |
| 2006/0264384 A1 | 11/2006 | Johansen et al. | |

FOREIGN PATENT DOCUMENTS

WO  WO 2008122038 A1 * 10/2008

OTHER PUBLICATIONS

Gupta et. al., Cancer Treatment Reviews, 2008, Elsevier, vol. 34, pp. 193-205.*
Reardon et. al., The Oncologist-NeuroOncology, 2006, Elsevier, vol. 11, pp. 152-164.*
http://www.cancer.gov/cancertopics/types/alphalist/y.*
Chabner et. al., Nature Reviews Cancer, 2005, Nature Publishing Group, vol. 5, pp. 65-72.*
Leaf, Fortune, 2004, ProQuest, vol. 149, issue 6, pp. 1-29 (pp. 76-97 online).*
Rich et. al., Nature Reviews Drug Discovery, 2004, Nature Publishing Group, vol. 3, pp. 430-446.*
Li et. al., The Lancet, 2004; Williams and Wilkins, vol. 363, pp. 1049-1057.*
Shi et. al., Bioorganic and Medicinal Chemistry Letters, 2008, Elsevier, vol. 18, pp. 3364-3368.*
Suzuki et. al., Journal of Medicinal Chemistry, 1997, American Chemical Society, vol. 40, pp. 2047-2052.*
http://www.cancer.org/cancer/kidneycancer/detailedguide/kidney-cancer-adult-what-is-kidney-cancer.*
DiPaolo et al., "Monitoring Antitumor Efficacy of Rapamycin in Kaposi Sarcoma", American Journal of Kidney Disease, Mar. 2007, 49(3), 462-470.
Dutcher, "Mammalian target of rapamycin inhibition", Clinical Cancer Research, Sep. 15, 2004, Access date Feb. 28, 2012, 10(18), 6382S-6387S.
Fan et al., "Chloroquine inhibits cell growth and induces cell death in A549 lung cancer cells", Bioorganic & medicinal chemistry, May 1, 2006, 14(9), 3218-3222.
Guertin et al., "An expanding role for mTOR in cancer", Trends in Molecular Medicine, Aug. 2005, 11(8), 353-361.
Kremer, "Rational use of new and existing disease-modifying agents in rheumatoid arthritis", Annals Internal Medicine, Apr. 17, 2001, 134(8), 695-706.
Lum et al., "Autophagy in metazoans: cell survival in the land of plenty", Nature Reviews Molecular Cell Biology, Jun. 2005, 6(6), 439-448.
Lum et al., "Growth factor regulation of autophagy and cell survival in the absence of apoptosis", Cell, Jan. 28, 2005, 120(2), 237-248.
Matthew et al., "Role of Autophagy in Cancer", Nature Review Cancer, Dec. 1, 2007, 7(12), 15 pages.
O'Neill et al., "4-Aminoquinolines—past, present, and future: a chemical perspective", Pharmacology and Therapeutics, Jan. 1998, 77(1), 29-58.
Romano et al., "Rapamycin inhibits doxorubicin-induced NF-kappaB/Rel nuclear activity and enhances the apoptosis of melanoma cells", European Journal of Cancer, Dec. 2004, 40(18), 2829-2836.
Sotelo et al., "Adding Chloroquine to Conventional Treatment for Glioblastoma Multiforme: A Randomized, Double-Blind, Placebo-Controlled Trial", Annals of Internal Medicine, Mar. 7, 2006, 144(5), 337-343.
Tourneau et al., "mTORC1 inhibitors: is temsirolimus in renal cancer telling us how they really work?", British Journal of Cancer, Oct. 14, 2008, 99(8),1197-1203.
Bray, K. et al., "Autophagy Suppresses RIP Kinase-Dependent Necrosis Enabling Survival to mTOR Inhibition," PLoS ONE, Jul. 2012, 7(7), e41831, 13 pages.
Rosich, L. et al., "Counteracting Autophagy Overcomes Resistance to Everolimus in Mantle Cell Lymphoma," Clinical Cancer Research, Aug. 9, 2012, 18, 5278-5289.
Xie, Xiaoqi et al., "Coordinate Autophagy and mTOR Pathway Inhibition Enhances Cell Death in Melanoma," PLoS ONE, Jan. 30, 2013, 8(1), e55096, 11 pages.

* cited by examiner

*Primary Examiner* — Sarah Pihonak
(74) *Attorney, Agent, or Firm* — Baker & Hostetler LLP (57) ABSTRACT

The present invention is directed to methods of using a sirolimus drug and chloroquine or a quinoline derivative in combination. Methods of use are also described.

12 Claims, 3 Drawing Sheets

COMBINATION ANTINEOPLASTIC THERAPY

CROSS-REFERENCE TO RELATED APPLICATIONS

This application is the National Stage of International Application No. PCT/US2010/033514, filed May 4, 2010, which claims the benefit of U.S. Provisional Application No. 61/177,697, filed May 13, 2009, the disclosures of which are incorporated herein by reference in their entireties.

TECHNICAL FIELD

The invention is directed to methods of treating cancer using a sirolimus compound and a chloroquine derivative.

BACKGROUND

Sirolimus, also known as rapamycin and marketed in the United States under the tradename RAPAMUNE® (Wyeth, Collegeville, Pa.), is currently indicated for the prevention of organ rejection after kidney transplant. Rapamycin derivatives useful for prevention of organ rejection have also been developed. For example, everolimus, marketed in the United States under the tradename CERTICAN® (Novartis, East Hanover, N.J.) is indicated for the prevention of organ rejection after heart or kidney transplantation.

Rapamycin has demonstrated anti-proliferative effects and has been shown to inhibit the progression of dermal Kaposi's sarcoma in patients with kidney transplants. S. DiPaolo, et al. Monitoring Antitumor Efficacy of Rapamycin in Kaposi Sarcoma, *American Journal of Kidney Diseases*, vol. 49, issue 3, 462-470. Rapamycin, in combination with doxorubicin, has been investigated for the treatment of melanoma. M. Romano, et al. Rapamycin inhibits doxorubicin-induced NF-kB/Rel nuclear activity and enhances the apoptosis of melanoma cells, *European Journal of Cancer*, vol. 40, issue 18, 2829-2836. Such data has prompted researchers to investigate the anti-proliferative potential of rapamycin and its derivatives. For example, temsirolimus, marketed in the United States under the tradename TORISEL® (Wyeth, Collegeville, Pa.), is currently indicated for the treatment of advanced renal cell carcinoma. Deforolimus is currently in Phase 2 clinical studies to evaluate deforolimus in patients with breast, endometrial, prostate cancer, and non-small cell lung cancer. While these rapamycin derivatives have demonstrated efficacy in treating some types of cancer, more research and development is needed to improve efficacy and response and survival rates.

Chloroquine is a 4-amino-substituted quinoline that has been used for over 60 years for malaria prophylaxis and treatment, rheumatoid arthritis treatment, and HIV treatment. Chloroquinoline derivatives such as hydroxylchloroquine are used to treat rheumatoid arthritis and systemic lupus erythematosis. Recent studies indicate that chloroquine may inhibit cell growth and may induce cell death in lung cancer cells. C. Fan, et al. *Bioorg. Med. Chem.* 2006 May 1; 14(9):3218-22. In 2006, researchers reported that adding chloroquine to standard chemotherapy and radiotherapy regimes for glioblastoma multiforme might improve survival rates of cancer patients receiving standard chemotherapy and radiotherapy. *Annals of Internal Medicine*, 7 Mar. 2006, vol. 144, issue 5, 1-31.

To date, there have been no reports of treating cancer in patients using a combination of a sirolimus drug and chloroquine or substituted quinoline.

SUMMARY

The present invention is directed to methods of simultaneously inducing and impairing the completion of cancer cell autophagy in a patient having or suspected of having a neoplasm. The invention comprises co-administering to the patient a sirolimus drug together with a substituted quinoline, the amounts of said sirolimus drug and substituted quinoline, in combination, being effective for limiting the growth and proliferation. This combination effect can be measured, for example, by an increase in autophagic vesicles in tumor tissue or surrogate tissue as compared to pretreatment samples or treatment with either a sirolimus drug or substituted quinoline alone. Also within the scope of the invention are methods of treating cancer in a patient comprising administering to the patient a therapeutically effective amount of a sirolimus drug and chloroquine or a substituted quinoline. Pharmaceutical compositions and kits are also described.

DETAILED DESCRIPTION OF ILLUSTRATIVE EMBODIMENTS

While both sirolimus and chloroquine have been reported to independently exhibit antitumor activity, prior to the present disclosure, there have been no reports of methods of treating cancer using a combination of a sirolimus drug and chloroquine (or a substituted quinoline). As set forth herein, the effects of the combination of a sirolimus drug and chloroquine (or a substituted quinoline) results in an inhibition of cancer cell growth that is greater than the sum of the inhibition of the individual molecules. That is, the combination of a sirolimus drug and chloroquine (or a substituted quinoline) results in cancer cell growth inhibition that is greater than one skilled in the art would have expected, based on the cancer cell inhibition effects of the sirolimus drug and chloroquine (or substituted quinoline) independently.

While not wishing to be bound to any particular theory, it is postulated that the combination of the sirolimus drug and chloroquine (or a substituted quinoline) results in simultaneous induction of autophagy (likely induced by the sirolimus drug) and impairment of the clearance of accumulating autophagic vesicles (likely impaired by the chloroquine or substituted quinoline) leading to the accumulation of a greater number of ineffective autophagosomes, followed by cell death.

As used herein, "a sirolimus drug" refers to a drug that is sirolimus, also known as rapamycin, or a sirolimus derivative:

Sirolimus (Rapamycin)

Sirolimus derivatives are known in the art and include, for example, everolimus, deforolimus, temisirolimus, and zotarolimus:

Everolimus

Deforolimus

Temisirolimus

Zotarolimus

Sirolimus drugs are inhibitors of the mammalian target of rapamycin (mTOR), also known as FK506 binding protein 12-rapamycin associated protein 1 (FRAP1). mTor is a serine/threonine protein kinase that regulates, for example, cell growth, cell proliferation, cell motility, cell survival, protein synthesis, and transcription.

As used herein, "chloroquine" refers to the following compound:

Chloroquine

As used herein, "substituted quinoline" refers to chloroquine derivatives wherein one or more hydrogens or functional groups of the chloroquine molecule have been replaced by one or more substituents that is, for example, halogen, $C_{1-10}$alkyl, —$OC_{1-10}$alkyl, —OH, $C_{6-10}$aryl, heteroaryl, heterocycloalkyl, alkheterocycloalkyl, heteroalkyl, alkylheteroalkyl. Exemplary embodiments of such substituted quinolines include, for example, hydroxychloroquine, amodiaquine, amopyroquine, cycloquine, tebuquine, bis pyroquine, sontoquine, primaquine, quinacrine, a mixture thereof, or pharmaceutically acceptable salts, enantiomers, or prodrugs thereof.

Also within the scope of the term "substituted quinoline" are quinoline-based compounds substituted by one or more substitutents that is, for example, halogen, $C_{1-10}$alkyl, —$C_{2-6}$alkenyl, —$OC_{1-10}$alkyl, —OH, $C_{6-10}$aryl, heteroaryl, heterocycloalkyl, heterocycloalkylalkyl, heteroalkyl, heteroalkylalkyl, haloalkyl. Exemplary embodiments of such substituted quinolines include, for example, mefloquine, quinine, a mixture thereof, or pharmaceutically acceptable salts, enantiomers, or prodrugs thereof.

As used herein, halogen refers to —F, —Cl, or —Br.

As used herein, "$C_{1-10}$alkyl" refers to a saturated straight, branched, cyclic, or multicyclic hydrocarbon having from 1 to 10 carbon atoms (and all combinations and sub combinations of ranges and specific numbers of carbon atoms therein). Alkyl groups include, but are not limited to, methyl, ethyl, n-propyl, isopropyl, cyclopropyl, n-butyl, isobutyl, t-butyl, cyclobutyl, n-pentyl, cyclopentyl, isopentyl, neopentyl, n-hexyl, isohexyl, cyclohexyl, cycloheptyl, cyclooctyl, decahydronaphthalenyl, adamantyl, 3-methylpentyl, 2,2-dimethylbutyl, and 2,3-dimethylbutyl. Alkyl groups can be substituted or unsubstituted.

As used herein, "heterocycloalkyl" refers to a non-aromatic heterocyclyl group where one or more of the ring forming carbon atoms is replaced by a heteroatom such as O, N, or S. Ring-forming carbon and heteroatoms such as S and N can further be oxidized in a heterocycloalkyl moiety. For example, the heterocycloalkyl can bear or two oxo, sulfido, or nitroxide moieties. In some embodiments, heterocycloalkyl groups have 3 to a bout 20 ring-forming atoms, preferably, 3, 4, 5, 6, or 7 ring forming atoms. Heterocycloalkyl groups include, but are not limited to piperazinyl, morpholinyl, tetrohydropyranyl, tetrahydrofuranyl, piperidinyl, pyrrolidinyl, oxazolinyl, and the like. Heterocycloalkyl groups can be substituted or unsubstituted.

As used herein, "heteroalkyl" refers to an alkyl group in which one or more hydrogen atoms is replaced by a heteroatom that is N, O, P or S. Heteroalkyl groups can be substituted or unsubstituted.

As used herein, "$C_{2-6}$alkenyl" refers to an alkyl group having one or more double bonds.

As used herein, "$C_{6-14}$aryl" refers to mono-, di-, tri-, or other multicyclic aromatic ring system having from 6 to 14 carbon atoms (and all combinations and subcombinations of ranges and specific numbers of carbon atoms therein). Non-limiting examples include phenyl, naphthyl, anthracenyl, and phenanthrenyl. Aryl groups can be substituted or unsubstituted.

As used herein, "heteroaryl" refers to a mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrrolyl, furyl, pyridyl, 1,2,4-thiadiazolyl, pyrimidinyl, isothiazolyl, thiazolyl, triazolyl, imidazolyl, tetrazolyl, pyrazinyl, quinolyl, isoquinolyl, thiophenyl, benzothienyl, isobenzofuryl, pyrazolyl, indolyl, purinyl, carbazolyl, benzimidazolyl, oxazolyl, and isoxazolyl. Heteroaryl groups can be substituted or unsubstituted.

As used herein, "haloalkyl" means an alkyl group substituted with one or more halogen groups selected from —F or —Cl.

Typically, substituted chemical moieties include one or more substituents that replace hydrogen. Exemplary substituents include, for example, halo (e.g., —F, —Cl, —Br), (provided that when halo is —Br, the —Br is attached to an $sp^2$ carbon such as on a carbon of an alkenyl or a ring carbon of aryl or heteroaryl group), alkoxy, haloalkoxy, —$OCF_3$, alkylthio, monohaloalkylthio, polyhaloalkylthio, —$SCF_3$, alkyl, —$CF_3$, haloalkyl, lower alkyl, spiroalkyl, alkenyl, alkynyl, aralkyl, aryl, heteroaryl, heterocyclyl, hydroxyl (—OH), nitro (—$NO_2$), cyano (—CN), sulfonyl (—$SO_2R^4$), sulfamoyl (—$SO_2NR^5R^6$), —$SR^4$, amino (—$NH_2$, $NHR^5$, $NHR^6$, $N(R^5R^6)$ and the like.

As used herein, "effective amount" refers to an amount of a compound as described herein that may be effective to inhibit, or treat the symptoms of cancer.

As used herein, "treating" refers to the palliative treatment of a condition, for example, cancer, and includes, in particular, not only the treatment of the condition per se, but also the prevention of the progression of the condition.

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

"Neoplasm" refers to lump, tumor, or leukemia characterized by an abnormal proliferation of cells.

"Patient" refers to an animal, including a mammal, preferably a human.

In some embodiments, the pharmaceutical compositions of the invention further comprise a pharmaceutically acceptable carrier or diluent. Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers and/or diluents are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Oral formulations are preferred. Formulations for oral or injected use are based on sufficient solubility as to allow the therapeutic agent to enter solution in the stomach or in an injectable medium. Suitable drug formulations include, but are not limited to, tablets, pills, capsules, sachets, granules, powders, chewing gums, suspensions, emulsions, suppositories, and solutions. Particularly preferred for oral use are tablets and capsules of all varieties and microbe-free solutions for injection or infusion. Where appropriate and necessary the formulations may include diluents, binding agents, dispersing agents, surface-active agents, lubricating agents, coating materials, flavoring agents, coloring agents, controlled release formulations, sweeteners or any other pharmaceutically acceptable additives, for example, gelatin, sodium starch glycolate, lactose, starch, talc, magnesium stearate, microcrystalline cellulose, Povidone, hydrogenated or unsaturated oils, polyglycols, syrups or other aqueous solutions. Where the formulations are tablets or capsules and the like the formulations may be presented as premeasured unit doses or in multidose containers from which the appropriate unit dose may be withdrawn.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

The injectable form may be an aqueous or nonaqueous solution, suspension or emulsion in a pharmaceutically acceptable liquid, e.g. sterile pyrogen-free water or parenterally acceptable oils or mixture of liquids which may contain bacteriostatic agents, antioxidants or other preservatives and stabilizers, buffers (preferably but not limited to a physiological pH range of 6.5-7.7, solutes to render the solution isotonic with the blood, thickening agents, suspending agents or other pharmaceutically acceptable additives. Such forms will be presented in unit dose form such as ampules or disposable injection devices or in multi-dose forms such as a bottle from which the appropriate dose may be withdrawn, or as a solid form or concentrate that can be used to quickly prepare an injectable formulation. All formulations for injection are preferable as sterile and pyrogen free. Suppositories containing the compound will also contain suitable carriers, e.g. cocoa butter, polyglycols or other state-of-the-art carriers.

Preferably the pharmaceutical composition is in single unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

When the combination products are not formulated together in a single dosage form, the sirolimus drug and chloroquine, or substituted quinoline, may be administered at the same time or simultaneously (that is, together), or in any order.

In addition to standard pharmaceutical additives there may be included within formulations of the compound other therapeutic agents.

The dosage of the composition of the present invention that will be most suitable for prophylaxis or treatment will vary with the form of administration, the particular compounds chosen and the physiological characteristics of the particular patient under treatment. Generally, small dosages may be used initially and, if necessary, increased by small increments until the desired effect under the circumstances is reached.

Generally speaking, oral administration may require higher dosages.

Preferably, administration of the combination products of the invention is oral, although other routes of administration, as described above, are contemplated to be within the scope of the present invention. Although it is preferable that the sirolimus drug and chloroquine, or substituted quinoline, are all administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the pharmaceutical composition of this invention will be readily ascertainable by one skilled in the art, once armed with the present disclosure, by way of general guidance, typically a daily dosage may range from about 0.015 to about 1500 milligrams of the chloroquine or the substituted quinoline (and all combinations and subcombinations of ranges therein) and about 0.001 to about 1000 milligrams of the sirolimus drug (and all combinations and subcombinations of ranges therein) per kilogram of patient body weight.

Particularly when provided as a single dosage form, the potential exists for a chemical interaction between the combined active ingredients. For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-pareils, which are then enteric coated. These enteric-coated microtablets, particles, granules or non-pareils are then placed into a capsule or compressed into a capsule along with a granulation of the other active ingredient.

In addition to providing for dosage forms wherein the pharmaceutically active components are presented in a single unit dosage form, kits including, for example, the sirolimus drug and the chloroquine (or substituted quinoline) as individual components of the kit is also envisioned. For example, one component of the kit can include a sirolimus drug and a first pharmaceutically acceptable carrier, diluent, or excipient. Another component of the kit can include chloroquine or a chloroquine derivative and a second pharmaceutically acceptable carrier, diluent, or excipient. In such embodiments, each component of the invention can be presented together in, for example, a push-through or peel-open blister pack. Other components of the kit may include implements for administering each individual active component, for example, syringes, if the active component or components are to be administered by injection.

The present invention is further defined in the following Examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Materials and Methods

Reagents and constructs: rapamycin (sirolimus, "rapa") and chloroquine (CQ) were purchased from Sigma-Aldrich, Inc (St. Louis, Mo.). The pC1-EGFP-LC3 vector was contributed by Dr. Mizushima (Japan).

Cell lines, transfection, and cell counting: LN229 cells were grown in DMEM supplemented with 10% heat-inactivated fetal bovine serum (Gemini Biosciences, Woodland, Calif.), 10 units/ml penicillin/streptomycin, and 2 mM L-glutamine (Invitrogen Corporation). LN229 cells were transfected with lipofectamine 2000 (Invitrogen) according to manufacturer protocol. Stable transfectants were selected with neomycin (Gibco), and high fluorescence clones of LN229 GFP-LC3 were selected by limiting dilution. For all in vitro experiments media+supplements and drugs treatments were changed daily. Cell number was assessed by using a Coulter Z2 particle analyzer and confirmed by trypan blue exclusion.

Figure 1:
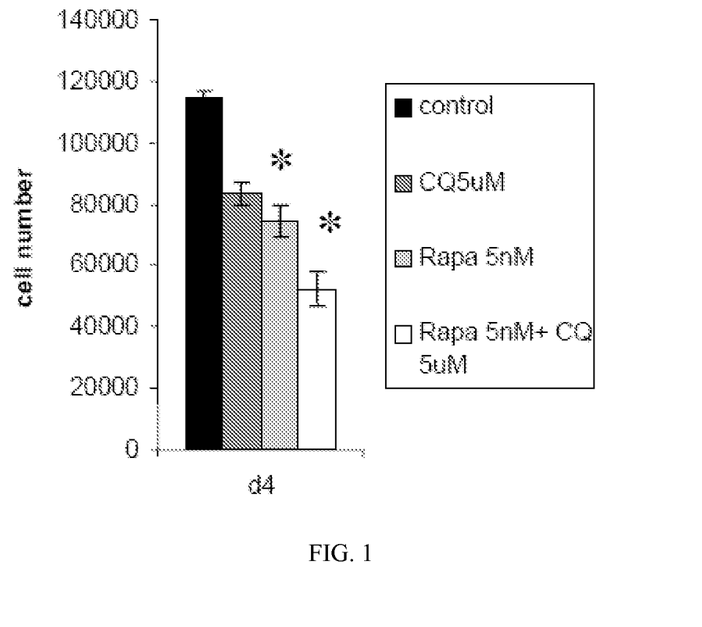
FIG. 1 depicts cell numbers of LN229 cells expressing GFP-LC3 after treatment with sirolimus ("rapa"), chloroquine (CQ), and the combination of rapamycin and chloroquine.

As depicted in FIG. 1, a combination of 5 nM rapamycin and 5 µM chloroquine resulted in a decrease in cell number. The decrease in cell number resulting from the combination of rapamycin and chloroquine was greater than the decrease in cell number observed with either rapamycin or chloroquine alone.

Fluorescence Microscopy: Cells were grown in sterile glass coverslips and treated in full medium as indicated above. After 48 hours of treatment cells were fixed with 4% paraformaldehyde and imaged using a Nikon upright fluorescent microscope. Images were captured at 100× and representative images were reported.

Figure 2:
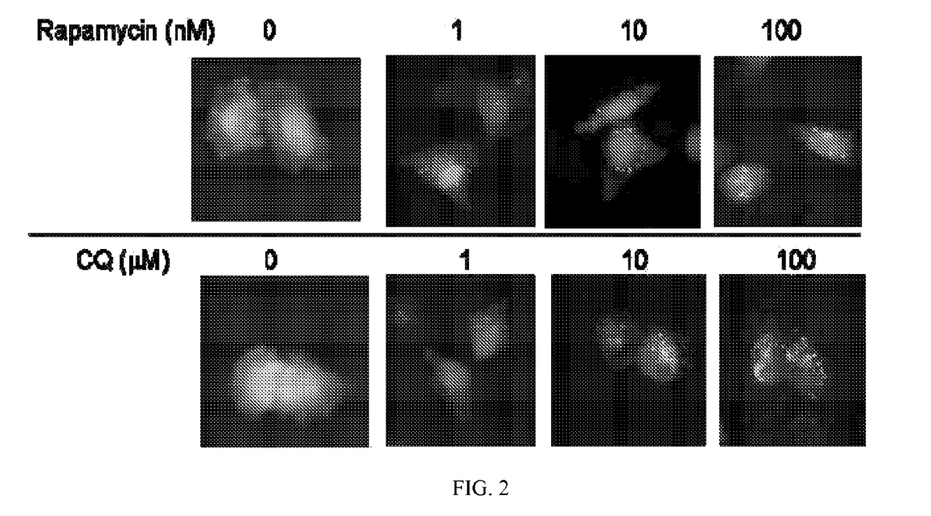
FIG. 2 depicts digital flouresence images of LN229 GFP-LC3 cells exposed to increasing doses of rapamycin (top) and chloroquine (CQ) (bottom). Punctate flouresence indicates the accumulation of LC3-positive autophagosomes.

As depicted in FIG. 2, LN229 cells, when treated with increasing doses of either rapamycin (top) or chloroquine (bottom) accumulated LC3-positive autophagosomes.

Electron Microscopy: Cells were fixed with 2.5% glutaraldehyde/2% formaldehyde with 0.1 M sodium cacodylate and stored at 4° C. until embedding. Cells were postfixed with 2% osmium tetroxide followed by an increasing gradient dehydration step using ethanol and propylene oxide. Cells were then embedded in LX-112 medium (Ladd) and sections were cut ultrathin (90 nm), placed on uncoated copper grids, and stained with 0.2% lead citrate and 1% uranyl acetate. Images were examined with a JEOL-1010 electron microscope (JEOL) at 80 kV. Cells were considered non-apoptotic if the integrity of the nuclear and cytoplasmic membrane were maintained. Autophagic vesicles were identified as double-membrane vesicles.

Figure 3:
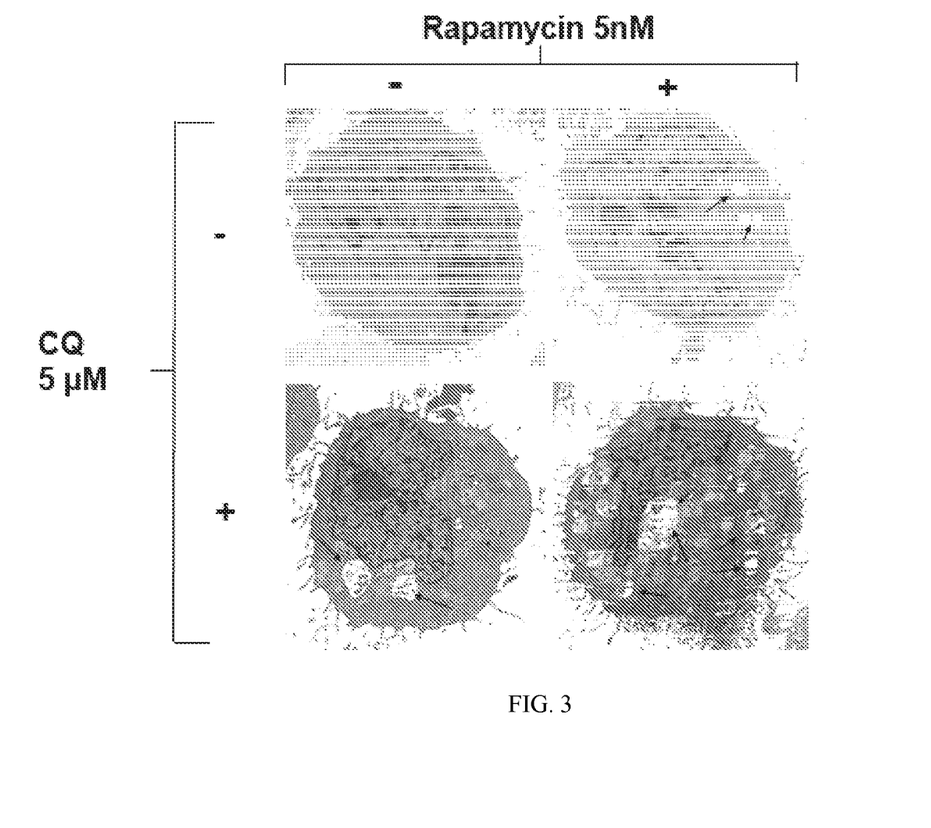
FIG. 3 depicts electron micrographs of LN229 GFL-LC3 cells untreated and treated with rapamycin, chloroquine (CQ), and a combination of rapamycin and chloroquine. Top left panel depicts untreated sample. Top right panel depicts treatment with rapamycin only. Lower left panel depicts treatment with chloroquine only. Lower right panel depicts treatment with both rapamycin and chloroquine. "↑" identify autophagosomes.

FIG. 3 depicts the electron micrographs of LN229 GFP-LC3 cells treated with either rapamycin, chloroquine, or the combination. While autophagosomes are observed when cells are treated with either rapamycin or chloroquine alone, the combination of rapamycin and chlorquine results in a greater number of autophagosomes.

What is claimed is:

1. A method of limiting the growth and proliferation of a cancer that is renal cell carcinoma or glioblastoma in a patient having or suspected of having renal cell carcinoma or glioblastoma comprising:
co-administering to the patient a sirolimus drug together with chloroquine, the amounts of said sirolimus drug and chloroquine, in combination, being effective for achieving said limiting of growth and proliferation.

2. The method of claim 1, wherein the limiting is achieved by modulating autophagy in the cancer cells.

3. The method of claim 1 wherein the sirolimus drug is sirolimus.

4. The method of claim 1 wherein the administration is concurrent.

5. The method of claim 1 wherein the administration is sequential.

6. The method of claim 1 wherein the sirolimus drug is temsirolimus.

7. A method of treating renal cell carcinoma or glioblastoma in a patient comprising administering to the patient a therapeutically effective amount of
a sirolimus drug; and
chloroquine.

8. The method of claim 7 comprising administration of sirolimus and chloroquine.

9. The method of claim 7 comprising administration of temsirolimus and chloroquine.

10. The method of claim 7 comprising administration of deforolimus, everolimus, temsirolimus, or zotarolimus and chloroquine.

11. The method of claim 7 wherein the administration is concurrent.

12. The method of claim 7 wherein the administration is sequential.

* * * * *

UNITED STATES PATENT AND TRADEMARK OFFICE
CERTIFICATE OF CORRECTION

PATENT NO. : 8,716,307 B2 Page 1 of 1
APPLICATION NO. : 13/319604
DATED : May 6, 2014
INVENTOR(S) : Amaravadi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 58 days.

Signed and Sealed this
Twenty-ninth Day of September, 2015

Michelle K. Lee
*Director of the United States Patent and Trademark Office*